US011628298B2

(12) United States Patent
Yoon et al.

(10) Patent No.: US 11,628,298 B2
(45) Date of Patent: Apr. 18, 2023

(54) METHODS AND IMPLANTABLE MEDICAL DEVICES FOR AUTOMATIC ENTRY TO AN EXPOSURE MODE OF OPERATION UPON EXPOSURE TO A MAGNETIC DISTURBANCE

(71) Applicant: Medtronic, Inc., Minneapolis, MN (US)

(72) Inventors: Hyun J. Yoon, Vadnais Heights, MN (US); Michael L. Ellingson, St. Louis Park, MN (US); Wade M. Demmer, Coon Rapids, MN (US); Jonathan D. Edmonson, Blaine, MN (US); Matthew J. Hoffman, St. Paul, MN (US); Ben W. Herberg, Andover, MN (US); James D. Reinke, Maple Grove, MN (US); Todd J. Sheldon, North Oaks, MN (US); Paul R. Solheim, Blaine, MN (US); Alison M. Seacord, St. Louis Park, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 599 days.

(21) Appl. No.: 16/410,117

(22) Filed: May 13, 2019

(65) Prior Publication Data
US 2019/0262604 A1  Aug. 29, 2019

Related U.S. Application Data

(62) Division of application No. 15/142,814, filed on Apr. 29, 2016, now Pat. No. 10,286,209.

(51) Int. Cl.
*A61N 1/37* (2006.01)
*A61N 1/08* (2006.01)
*A61N 1/39* (2006.01)

(52) U.S. Cl.
CPC .............. *A61N 1/08* (2013.01); *A61N 1/3718* (2013.01); *A61N 1/3931* (2013.01)

(58) Field of Classification Search
CPC ....... A61N 1/08; A61N 1/3931; A61N 1/3718
See application file for complete search history.

(56) References Cited

U.S. PATENT DOCUMENTS 5,877,630 A    3/1999  Kraz
6,937,906 B2   8/2005  Terry et al.
(Continued)

FOREIGN PATENT DOCUMENTS

EP          1935450       6/2008
WO     2012134603 A1    10/2012

OTHER PUBLICATIONS

Yoon et al., "Methods and Implantable Medical Devices for Automatic Entry To an Exposure Mode of Operation Upon Exposure To a Magnetic Disturbance", EP Application No. 20156629.6, filed Apr. 27, 2017, Extended European Search Report, dated May 29, 2020, 7 pages.
(Continued)

*Primary Examiner* — Rex R Holmes
(74) *Attorney, Agent, or Firm* — Withers & Keys, LLC

(57) ABSTRACT

Implantable medical devices automatically switch from a normal mode of operation to an exposure mode of operation and back to the normal mode of operation. The implantable medical devices may utilize hysteresis timers in order to determine if entry and/or exit criteria for the exposure mode are met. The implantable medical devices may utilize additional considerations for entry to the exposure mode such as a confirmation counter or a moving buffer of sensor values. The implantable medical devices may utilize additional considerations for exiting the exposure mode of operation and returning to the normal mode, such as total time in the exposure mode, patient position, and high voltage source (Continued)

charge time in the case of devices with defibrillation capabilities.

8 Claims, 9 Drawing Sheets

(56) References Cited

U.S. PATENT DOCUMENTS

| | | | |
|---|---|---|---|
| 7,050,855 B2 | 5/2006 | Zeijlemaker et al. |
| 7,076,283 B2 | 7/2006 | Cho et al. |
| 7,212,863 B2 | 5/2007 | Strandberg |
| 7,509,167 B2 | 3/2009 | Stessman |
| 7,561,915 B1 | 7/2009 | Cooke et al. |
| 3,014,867 A1 | 9/2011 | Cooke et al. |
| 8,121,678 B2 | 2/2012 | Linder et al. |
| 8,335,563 B2 | 12/2012 | Stessman |
| 8,391,992 B2 | 3/2013 | Lyden et al. |
| 8,433,408 B2 | 4/2013 | Ellingson et al. |
| 8,437,862 B2 | 5/2013 | Yoon et al. |
| 8,467,882 B2 | 6/2013 | Ellingson et al. |
| 8,509,888 B2 | 8/2013 | Linder et al. |
| 8,543,207 B2 | 9/2013 | Cooke et al. |
| 8,744,578 B2 | 6/2014 | Ellingson |
| 8,805,496 B2 | 8/2014 | Ellingson |
| 8,886,317 B2 | 11/2014 | Cooke et al. |
| 9,095,721 B2 | 8/2015 | Stancer et al. |
| 9,138,584 B2 | 9/2015 | Stancer et al. |
| 2005/0043761 A1 | 2/2005 | Connelly et al. |
| 2006/0167496 A1 | 7/2006 | Nelson et al. |
| 2006/0293591 A1 | 12/2006 | Wahlstrand et al. |
| 2007/0255332 A1 | 11/2007 | Cabelka et al. |
| 2009/0157146 A1* | 6/2009 | Linder ............... A61N 1/37217 607/60 |
| 2010/0176808 A1 | 7/2010 | Legay |
| 2010/0198309 A1 | 8/2010 | Cabelka et al. |
| 2011/0106204 A1 | 5/2011 | Yoon et al. |
| 2011/0148400 A1 | 6/2011 | Doerr et al. |
| 2011/0178562 A1 | 7/2011 | Legay et al. |
| 2012/0108908 A1 | 5/2012 | Ellingson |
| 2012/0109260 A1* | 5/2012 | Stancer ............... A61N 1/39622 607/60 |
| 2013/0268012 A1 | 10/2013 | Sison |
| 2014/0139568 A1 | 2/2014 | Legay |
| 2014/0100624 A1 | 4/2014 | Ellingson |
| 2015/0352354 A1 | 12/2015 | Doerr et al. |

OTHER PUBLICATIONS (PCT/US2017/029758) PCT Notification of Transmittal of the International Search Report and the Written Opinion of the International Searching Authority, dated Dec. 13, 2017, 11 pages.

Chinese Application No. 201780026603.0 Office Action, dated Nov. 26, 2021.

European Application No. 20 156 629.6 Office Action, dated Jan. 2, 2023.

* cited by examiner

METHODS AND IMPLANTABLE MEDICAL DEVICES FOR AUTOMATIC ENTRY TO AN EXPOSURE MODE OF OPERATION UPON EXPOSURE TO A MAGNETIC DISTURBANCE

CROSS REFERENCE TO RELATED APPLICATIONS

This application is a Divisional of U.S. patent application Ser. No. 15/142,814, now U.S. Pat. No. 10,286,209, entitled "METHODS AND IMPLANTABLE MEDICAL DEVICES FOR AUTOMATIC ENTRY TO AN EXPOSURE MODE OF OPERATION UPON EXPOSURE TO A MAGNETIC DISTURBANCE," filed Apr. 29, 2016, the content of which is incorporated by reference in its entirety.

TECHNICAL FIELD

Embodiments relate to methods and implantable medical devices that allow for entry into an exposure mode of operation by the implantable medical device. More specifically, embodiments relate to automatic entry into the exposure mode by the implantable medical device upon being exposed to a magnetic disturbance.

BACKGROUND

Implantable medical devices may perform various functions in order to deliver modes of therapy to a patient. For example, cardiac stimulation devices like pacemakers and defibrillators may sense electrical physiologic signals in some modes of therapy in addition to providing electrical pacing signals to one or more chambers of the heart. Some modes of therapy that sense a physiologic signal then use that signal when determining how to control the pacing signal.

Patients that have an implantable medical device may be exposed to magnetic disturbances like those caused by MM scans or other medical procedures. These magnetic disturbances may result in the device sensing signals that are not actually physiologic but are artificially created by the magnetic disturbances. If the device is allowed to control the pacing signal based on the sensed artificial signal, then the pacing signal may be inappropriate or even harmful for the patient. Therefore, it is commonplace to utilize an exposure mode of therapy during such disturbances. For example, one type of exposure mode deactivates sensing or otherwise ignores the sensed signal and paces asynchronously in a pre-defined pacing configuration with a pre-defined pacing rate. Other types of exposure modes may also be used, such as triggered pacing by filtering externally produced noise from the sensed signal.

Conventionally, the exposure mode of operation is triggered by a clinician using an external device to communicate with the implantable medical device. For example, immediately prior to a patient having an implantable medical device entering an MRI scan, a clinician may program that implantable medical device to enter the exposure mode. Likewise, upon exiting the MRI scan, the clinician then programs the implantable medical device to switch back to a normal mode of operation.

This manual process of entering and exiting the exposure mode of operation presents potential issues. For instance, there is the possibility of human error. Should the fact that the patient has an implantable medical device not be recognized by the personnel responsible for the MRI scan, a clinician may not be present to program the device to enter the exposure mode. Even if the clinician is present, there could be a mistake in programming the device to enter the exposure mode. Furthermore, requiring the clinician to be present to program the device is an added expense to the MRI scan procedure.

SUMMARY

Embodiments address issues such as these and others by providing methods and implantable medical devices that allow for the implantable medical device to automatically enter an exposure mode of operation upon being exposed to a magnetic disturbance such as that from an MRI machine. Accordingly, there is no need to manually program the device prior to the MRI scan. Embodiments may additionally provide for automatically exiting the exposure mode and switching back to the normal mode of operation.

Embodiments provide a method of switching from a normal mode of operation to an exposure mode of operation for an implantable medical device. The method involves the implantable medical device, while in the normal mode of operation, periodically detecting whether a magnetic field sensor is producing a first signal level that suggests a magnetic disturbance is present. Once the magnetic field sensor produces the first signal level while the implantable medical device is in the normal mode of operation, the method involves starting an exit test cycle by setting a hysteresis timer to a hysteresis start value and switching to the exposure mode of operation. The method further involves continuing the exit test cycle by periodically detecting whether the magnetic field sensor produces the first signal level. When it is detected during the exit test cycle that the magnetic field sensor is producing the first signal level, the method involves setting the hysteresis timer to the hysteresis start value. When it is detected during the exit test cycle that the magnetic field sensor is not producing the first signal level, the method then involves adjusting the hysteresis timer by a unit toward the stop value, and when the hysteresis timer reaches the stop value during the exit test cycle, the method involves switching to the normal mode of operation.

Embodiments provide a method of switching from a normal mode of operation to an exposure mode of operation for an implantable medical device. The method involves the implantable medical device, while in the normal mode of operation, periodically detecting whether a magnetic field sensor is producing a first signal level that suggests a magnetic disturbance is present. Once the magnetic field sensor produces the first signal level while the implantable medical device is in the normal mode of operation, the method involves starting an entry test cycle by setting a hysteresis timer to a hysteresis start value and adjusting a confirmation counter by a unit from a confirmation start value toward a target value. The method further involves continuing the entry test cycle by periodically detecting whether the magnetic field sensor produces the first signal level. When it is detected during the entry test cycle that the magnetic field sensor is producing the first signal level, the method involves setting the hysteresis timer to the hysteresis start value and adjusting the confirmation counter by a unit toward the target value. When it is detected during the entry test cycle that the magnetic field sensor is not producing the first signal level, the method then involves adjusting the hysteresis timer by a unit toward the stop value and adjusting the confirmation counter by a unit toward the target value. When the hysteresis timer reaches the stop value during the entry test cycle, the method involves setting the confirmation counter back to the confirmation start value, and when the confirmation counter reaches the target value during the entry test cycle, the method involves switching to the exposure mode of operation.

Embodiments provide a method of switching between a normal mode of operation and an exposure mode of operation for an implantable medical device. The method involves the implantable medical device, while in the normal mode of operation, detecting over a first period of time a first aggregated amount of time that a magnetic field sensor signals that a magnetic disturbance is present. The method also involves comparing the first aggregated amount of time to a first threshold, and when the first aggregated amount of time exceeds the first threshold, the method then involves switching to the exposure mode of operation for the implantable medical device.

Embodiments provide an implantable medical device that includes a magnetic field sensor and a controller that selects between a normal mode of operation and an exposure mode of operation. The controller is configured to, while in the normal mode of operation, periodically detect whether the magnetic field sensor is producing a first signal level that suggests a magnetic disturbance is present. Once the magnetic field sensor produces the first signal level while the implantable medical device is in the normal mode of operation, the controller is configured to start an exit test cycle by setting a hysteresis timer to a hysteresis start value and switching to the exposure mode of operation. The controller is configured to continue the exit test cycle by periodically detecting whether the magnetic field sensor produces the first signal level. When it is detected during the exit test cycle that the magnetic field sensor is producing the first signal level, the controller sets the hysteresis timer to the hysteresis start value. When it is detected during the exit test cycle that the magnetic field sensor is not producing the first signal level, the controller adjusts the hysteresis timer by a unit toward the stop value. When the hysteresis timer reaches the stop value during the exit test cycle, the controller switches to the normal mode of operation.

Embodiments provide an implantable medical device that includes a magnetic field sensor and a controller that selects between a normal mode of operation and an exposure mode of operation. The controller is configured to, while in the normal mode of operation, periodically detect whether the magnetic field sensor is producing a first signal level that suggests a magnetic disturbance is present. Once the magnetic field sensor produces the first signal level while in the normal mode of operation, the controller is configured to start an entry test cycle by setting a hysteresis timer to a hysteresis start value and adjusting a confirmation counter by a unit from a confirmation start value toward a target value. The controller is configured to continue the entry test cycle by periodically detecting whether the magnetic field sensor produces the first signal level. When it is detected during the entry test cycle that the magnetic field sensor is producing the first signal level, the controller sets the hysteresis timer to the hysteresis start value and adjusts the confirmation counter by the unit toward the target value. When it is detected during the entry test cycle that the magnetic field sensor is not producing the first signal level, the controller adjusts the hysteresis timer by the unit toward the stop value and adjusts the confirmation counter by the unit toward the target value. When the hysteresis timer reaches the stop value during the entry test cycle, the controller sets the confirmation counter back to the confirmation start value. When the confirmation counter reaches the target value during the entry test cycle, the controller switches to the exposure mode of operation.

Embodiments provide an implantable medical device that includes a magnetic field sensor and a controller that selects between a normal mode of operation and an exposure mode of operation. The controller is configured to, while in the normal mode of operation, communicate with the magnetic field sensor to detect over a first period of time a first aggregated amount of time that the magnetic field sensor signals that a magnetic disturbance is present. The controller is further configured to compare the first aggregated amount of time to a first threshold and when the first aggregated amount of time exceeds the first threshold, the controller then switches to the exposure mode of operation for the implantable medical device.

This summary is intended to provide an overview of the subject matter described in this disclosure. It is not intended to provide an exclusive or exhaustive explanation of the techniques as described in detail within the accompanying drawings and description below. Further details of one or more examples are set forth in the accompanying drawings and the description below. Other features, objects, and advantages will be apparent from the description and drawings, and from the statements provided below.

DETAILED DESCRIPTION

Embodiments provide the ability for an implantable medical device to automatically enter and exit an exposure mode of operation when in the presence of a magnetic disturbance like that of an MRI machine. Accordingly, these embodiments may be used as a manner of streamlining the MRI process, avoiding the need for manual programming by a clinician to switch from a normal mode to the exposure mode and then back to the normal mode. Furthermore, one or more embodiments may serve as a fail-safe in situations where a clinician may still be used for manual programming should the clinician make a mistake.

Figure 1:
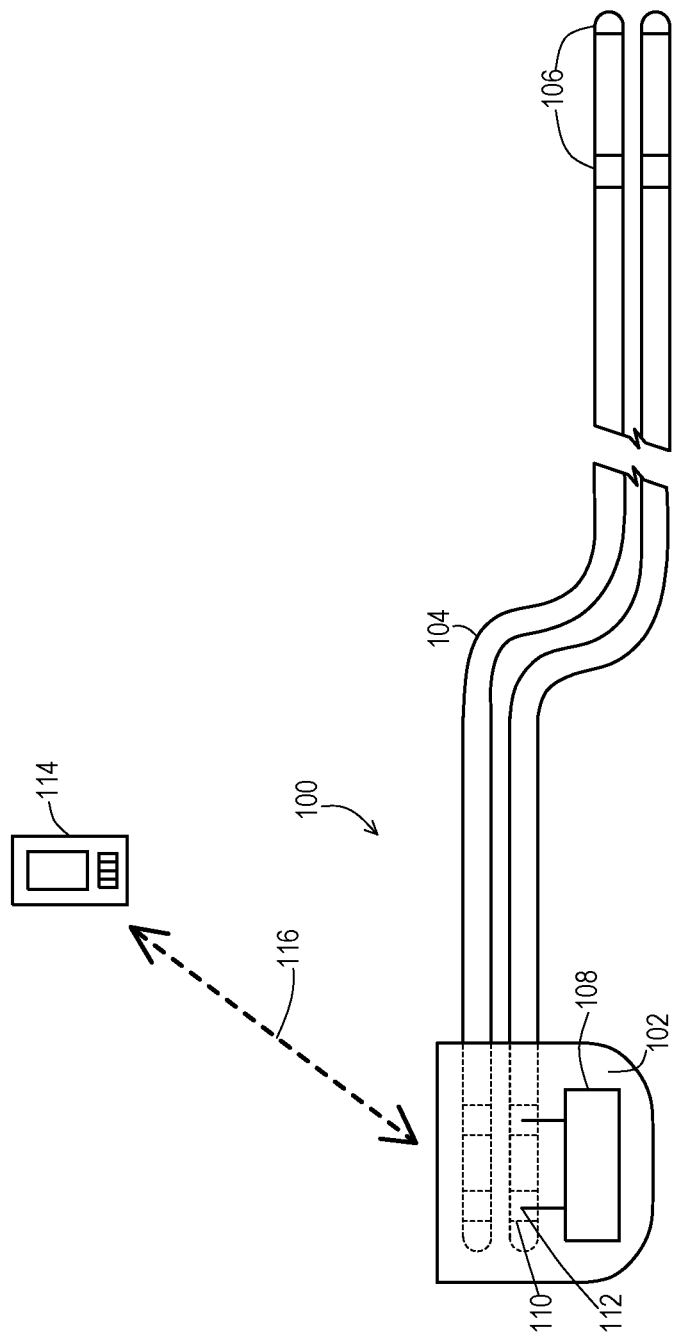
FIG. 1 shows an example of an implantable medical system that may operate according to various embodiments disclosed herein.

FIG. 1 shows an example of an implantable medical system according to embodiments disclosed herein. A patient receives an implantable medical system 100 which, in this example, implantable medical system 100 includes an implantable medical device 102 that has the ability to perform electrical sensing and pacing. The implantable medical device (IMD) 102 may be of various types and some of those types may offer additional functionality such as defibrillation and/or cardiac resynchronization therapy. The IMD 102 may even be primarily for non-pacing functions like defibrillation and/or cardiac resynchronization although may include the ability to pace if needed. A collection 108 of electrical components is included to provide these functions. Embodiments may include additional or entirely different functions as well.

The implantable medical system 100 in some cases may be without any electrical leads and as well as with one or more electrical leads 104. The electrical lead(s) 104 are electrically connected to the IMD 102 via proximal contacts 110 on the leads 104 and electrical connectors 112 of the IMD 102. The leads 104 include electrodes 106 on a distal end that interface with the body tissue to capture electrical physiologic signals or deliver electrical pacing signals.

Additionally, in some cases the implantable medical system 100 may include external devices 114 such as hand-held controllers that are capable of communicating wirelessly with the IMD 102. The wireless communications may be near field, arm's length, far field and the like as is shown in the art. The external device 114 may generate commands to the IMD 102 to request information about the IMD 102 and/or to instruct the IMD 102 to operate in a particular way. In particular, in some cases the external device 114 may be used to manually switch the IMD 102 to enter an exposure mode of therapy. However, the IMD 102 has the ability to automatically detect magnetic disturbances and then automatically enter and exit an exposure mode of therapy.

Figure 2:
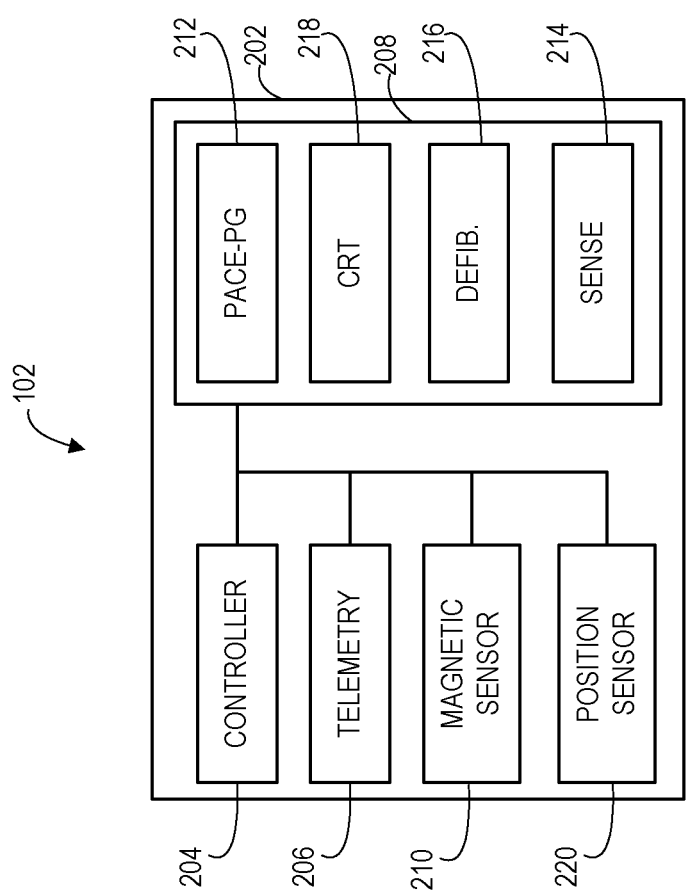
FIG. 2 shows an example of components of the implantable medical system.

FIG. 2 shows an example of components of an IMD 102. The IMD 102 may include a housing 202 that contains the various components. The IMD 102 includes a controller 204 that may control the operations of the IMD 102 by communicating with other components. The controller 204 may be of various forms such as a general purpose programmable processor, a dedicated purpose processor, hardwired digital logic, and the like. The controller 204 may also include internal or external memory having computer-readable instructions that, when executed by controller 204, cause controller 204 to perform various operations attributed to it in this disclosure. The memory may include any volatile, non-volatile, magnetic, optical, or electrical media, such as a random access memory (RAM), read-only memory (ROM), non-volatile RAM (NVRAM), static non-volatile RAM (SRAM), electrically-erasable programmable ROM (EEPROM), flash memory, or any other non-transitory computer-readable storage media.

The IMD 102 may include telemetry 206 to communicate wirelessly with external devices such as the external device 114. As discussed above, the IMD 102 may communicate via one or more types of wireless communications including near field, arm's length, far field and the like. For instance, the telemetry 206 may include inductive coupling for near field or arm's length, or may include radio frequency far field functions such as those operating in the Medical Implant Communication Service (MICS) band.

The IMD 102 also includes a therapy device 208 that may include one or more engines for providing various therapy functions. For instance, the therapy device 208 may include a configurable pacing engine 212 that may pace one or more chambers of the heart via corresponding electrodes 106 of the lead 104. The therapy device 208 may include a configurable sensing engine 214 to sense from one or more chambers of the heart. Likewise, depending upon the type of IMD 102, the therapy device 208 may include a defibrillation energy source 216 capable of providing high voltage defibrillation shocks. Again depending upon the type of IMD 102, the therapy device 208 may include a cardiac resynchronization engine 218 capable of providing cardiac resynchronization signals.

Additionally, the IMD 102 may include one or more magnetic field sensors 210 for detecting magnetic disturbances. For instance, Hall Effect sensors may be used to detect that a magnetic field of a particular intensity is present. This information from the sensor may be considered by the controller 204 when determining whether to enter or exit the exposure mode.

In some embodiments, the IMD 102 may also include a position sensor 220. An example of a position sensor 220 may be an accelerometer that has one or many axes of detection. The position sensor 220 provides information to the controller 204 regarding the physical position of the patient having the IMD 102, such as whether the patient is in a prone or supine position versus an upright position.

Examples of operations performed by the controller 204 are discussed below in relation to FIGS. 3-10. In each instance, the controller 204 communicates with the magnetic field sensor 210. In the example of FIG. 10, the controller 204 also communicates with the position sensor 220. Additionally, the controller 204 may implement timing mechanisms such as a hysteresis timer, a confirmation counter/timer, a moving buffer of time, and the like to accomplish the analysis for entering or exiting exposure mode.

Figure 3:
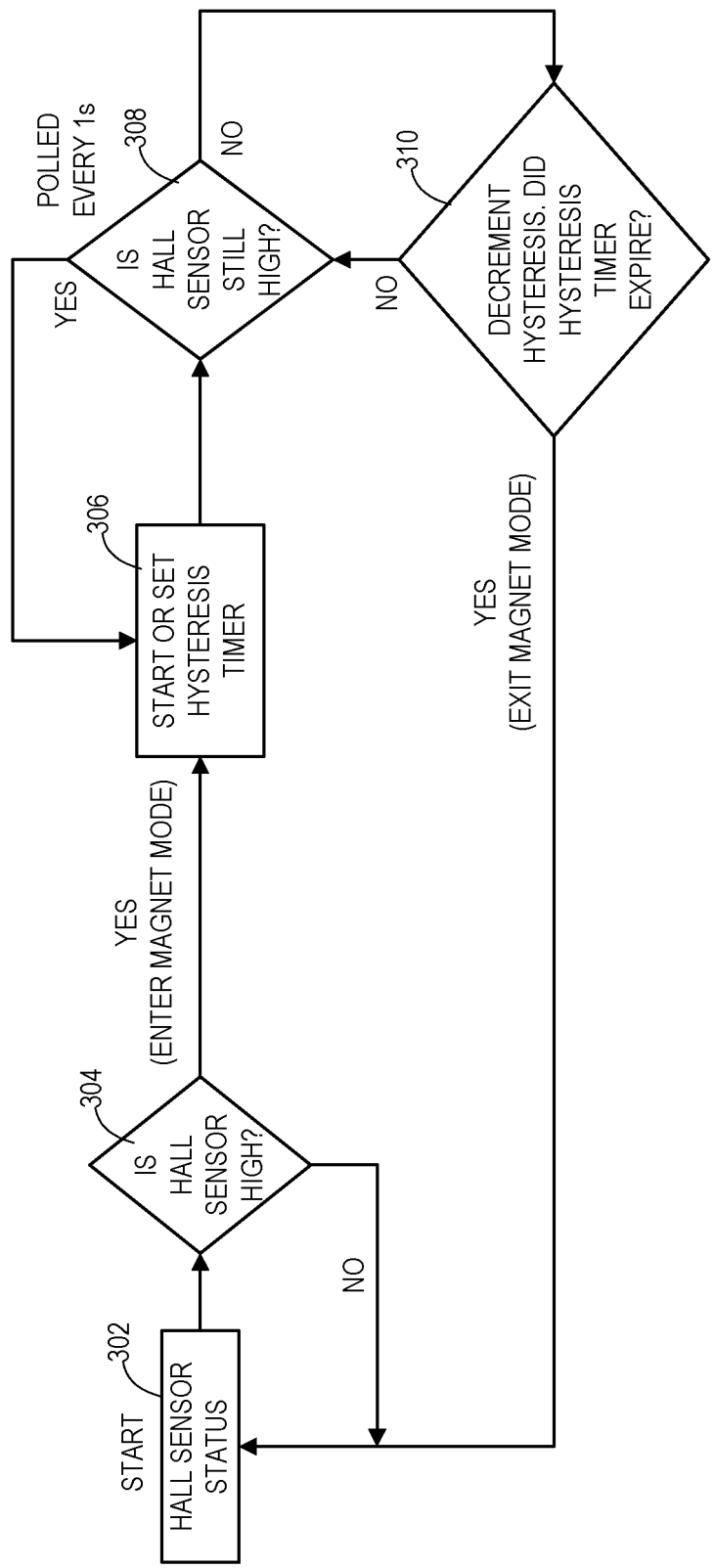
FIG. 3 shows one example of operations that may be performed by an implantable medical device to automatically enter an exposure mode of operation based on a magnetic field sensor and then automatically exit by using the magnetic field sensor together with a hysteresis timer.

FIG. 3 shows an example 300 of logical operations that may be implemented to quickly enter an exposure mode automatically, which in this example is referred to as a magnet mode that applies for both device programming and other magnetic related situations like MM scans. It will be appreciated, especially from further reading below in relation to FIG. 4, that examples may provide a magnet mode for programming purposes and then another exposure mode beyond magnet mode for such situations as an MRI scan.

The operations 300 begin at a status operation 302 where the controller 204 begins obtaining the status of the magnetic field sensor 210 on a periodic basis. For instance, the sensor 210 may be polled once every second. At a query operation 304, the controller 204 detects whether the sensor 210 is producing a signal that indicates that a magnetic field is present, for instance a HIGH state. If the sensor signal is not a HIGH state, which indicates no magnetic field is present, the status check simply repeats at the next polling time. However, when the sensor signal is HIGH, the controller 204 immediately enters the exposure mode (i.e., magnet mode in this example).

Once in the magnet mode, the controller 204 then starts a hysteresis timer at a start value, such as a maximum value for countdown purposes. In one example, the hysteresis timer may be set to 30 seconds while in another example the hysteresis timer may be set to some amount higher or lower than 30 seconds. 30 seconds has been found to be a practical example. Starting of the hysteresis timer then begins an exit test cycle where exit criteria may be examined repeatedly until it is determined that the device should exit the exposure mode and switch back to the normal mode of operation.

During this exit test cycle, the controller 204 continues to poll the sensor 210 and determine if the sensor 210 is in the HIGH state at a query operation 308. Each time that the sensor 210 is polled and returns a HIGH signal value, the controller 204 then sets the hysteresis counter back to its start value at the operation 306. Each time that the sensor 210 is polled and returns a non-HIGH signal value, the controller 204 then adjusts the hysteresis timer by a unit of time in the direction of a stop value (e.g., decrement by 1 second) and also determines if the hysteresis counter has expired by reaching the stop value. For instance, if the hysteresis start value is 30 seconds, the stop value may be zero such that the hysteresis counter must be decremented to zero in order to expire. If the hysteresis timer has not yet expired, then the sensor 210 is polled again at the next polling time at the query operation 308. However, once the hysteresis timer has expired at the query operation 310, the controller 204 then exits the exposure mode and switches back to the normal mode of operation.

In this manner, the device will remain in the exposure mode for at least the amount of time between the hysteresis timer start value and hysteresis timer stop value. To the extent the sensor 210 goes high one or more times after initially being in the HIGH state at the moment of switching to the exposure mode, then the exposure mode will persist even longer. This prevents rapid switching back and forth between the exposure mode and the normal mode of operation, which provides a steadier delivery of therapy to the patient but also accounts for sensor toggling that is typical during an MRI scan, especially during entry to and exit from the MRI scan room where patient movement relative to the MM machine causes sensor fluctuation. An example of this toggling is shown below in FIG. 7 in relation to the examples of FIGS. 8-10. However, this toggling is addressed by the example of FIG. 3 as well.

Figure 4:
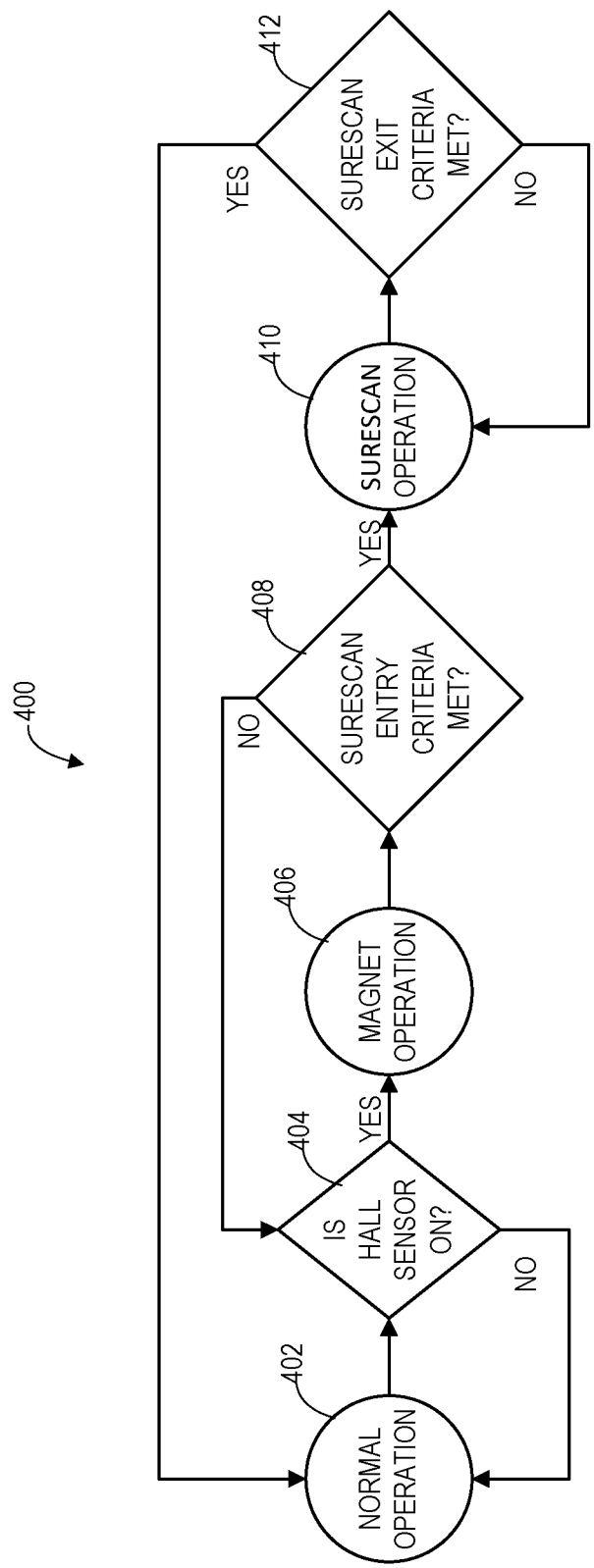
FIG. 4 shows an overview of operations that may be performed by an implantable medical device by utilizing entry and exit criteria to automatically enter and exit an exposure mode of operation.

FIG. 4 shows an example 400 of operations at a high level to illustrate the use of multiple modes to handle magnetic disturbance, where the exposure mode may have both entry and exit criteria for purposes of automatically switching modes. The device 102 has the normal mode state 402. When the sensor 210 provides a signal level (e.g., HIGH) that suggests a magnetic field is present, the device 102 may immediately enter the magnetic mode of operation 406, which may ready the device for programming.

Regardless of whether a magnet mode is used or not, once the sensor 210 provides the HIGH signal, the controller 204 begins an entry test cycle by assessing the entry criteria for entering the exposure mode at the query 408. If the entry criteria are not yet met, the entry test cycle continues by periodically polling the sensor 210. Once the entry criteria are met, the controller switches to the exposure mode of operation (also referred to herein as SureScan operation) at the exposure mode state 410. The controller then begins an exit test cycle by continuing to periodically poll the sensor 210 and assess whether exit criteria are met at a query operation 412. Once the exit criteria are met, the controller 204 then returns the device 102 to the normal mode of operation at the normal mode state 402.

Figure 5:
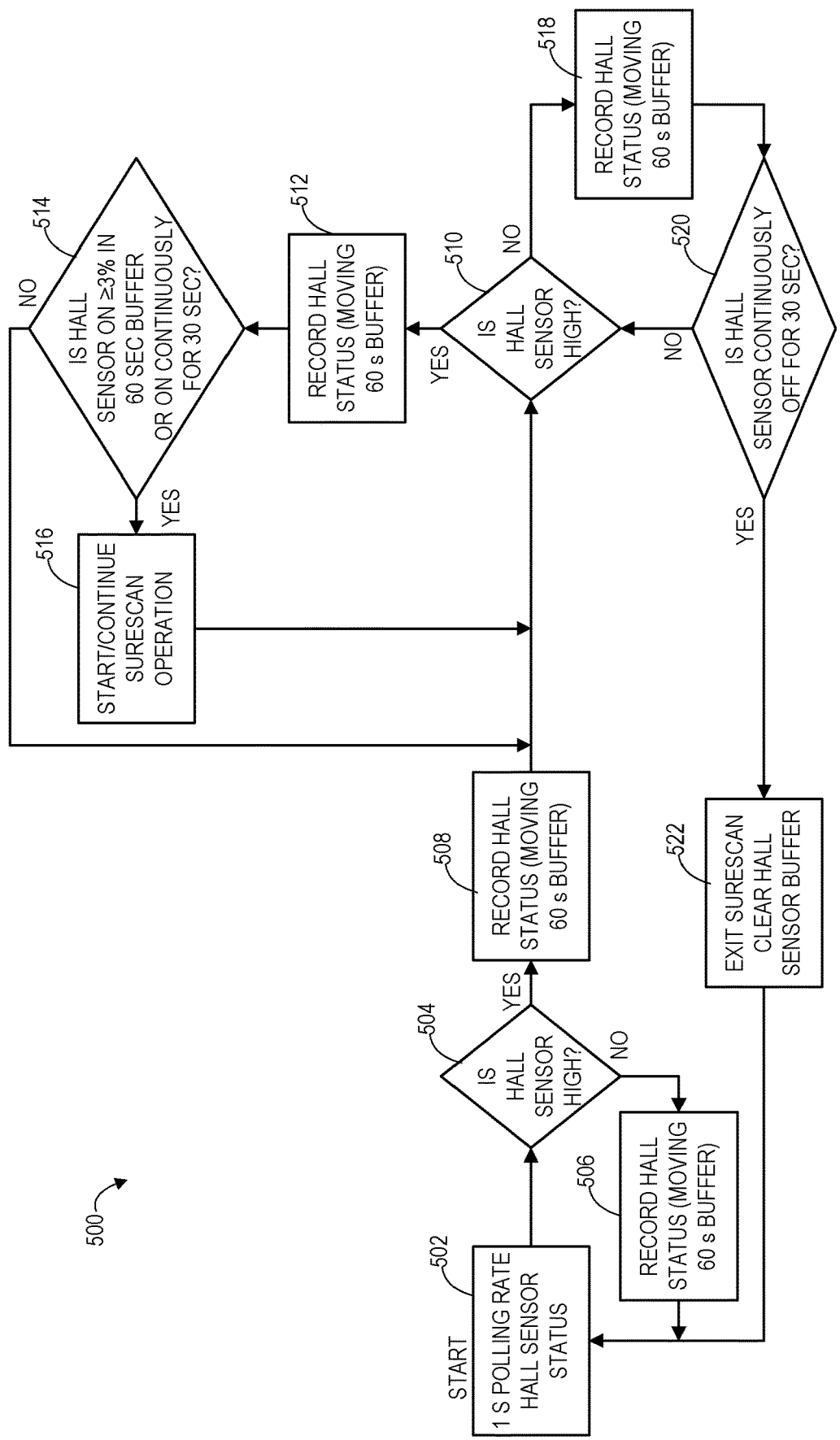
FIG. 5 shows one example of operations that may be performed by an implantable medical device to assess entry criteria and exit criteria in order to automatically enter and exit an exposure mode of operation.

FIG. 5 shows an example 500 of using entry and exit criteria. In this particular example, it is further recognized that the sensor 210 toggles during entry to and exit from the MRI scan room, and this phenomenon is used to trigger the exposure mode. Initially, the controller 204 is polling the sensor 210 at a polling interval such as one second while in the normal mode of operation at an operation 502. The controller 204 detects whether the signal from the sensor 210 is of a value such as HIGH that indicates that a magnetic field is present at a query operation 504. If not, then the controller 204 records the status for a moving buffer of some amount of time such as 60 seconds at an operation 506 and then polls the sensor 210 at the next polling time.

When the controller 204 determines that the signal is HIGH, then the controller 204 again records the sensor status within the moving 60 second buffer at an operation 508 and begins an entry test cycle by continuing to periodically poll the sensor 210. At a query operation 510, the controller 204 again detects if the sensor 210 is HIGH. When the sensor 210 is HIGH, the controller 204 records the status to the moving buffer at an operation 512. The controller 204 then determines whether the sensor 210 has been HIGH for an adequate amount of time within the moving buffer at a query operation 514 in order to determine whether switching to the exposure mode is appropriate. For example, the controller 204 may determine if the aggregated amount of time that the sensor 210 has been HIGH within the amount of time represented by the moving buffer meets a threshold. For instance, the controller 204 may determine if the sensor 210 has been HIGH for at least 3% of the time during the last 60 seconds. Additionally, or alternatively, the controller 204 may instead determine from the moving buffer whether the sensor 210 has been HIGH for a continuous amount of time such as 30 seconds. Once the entry criteria are met, the controller 204 then switches to the exposure mode at the operation 516.

Returning to query operation 510, if the sensor is not HIGH, the controller 204 again records the status to the moving buffer at an operation 518. The controller 204 then detects whether the sensor 210 has been off (i.e., non-HIGH) continuously for some threshold amount of time such as 30 seconds at a query operation 520. If the sensor has not been off continuously for the threshold amount of time, then polling continues at the query operation 510. If the sensor 210 has been off continuously for the threshold amount of time, then the controller 204 switches from the exposure mode back to the normal mode, if the device is currently in the exposure mode, and clears the moving buffer at an operation 522. The controller 204 then continues to poll the sensor 210 while in the normal mode of operation at the operation 502.

Figure 6:
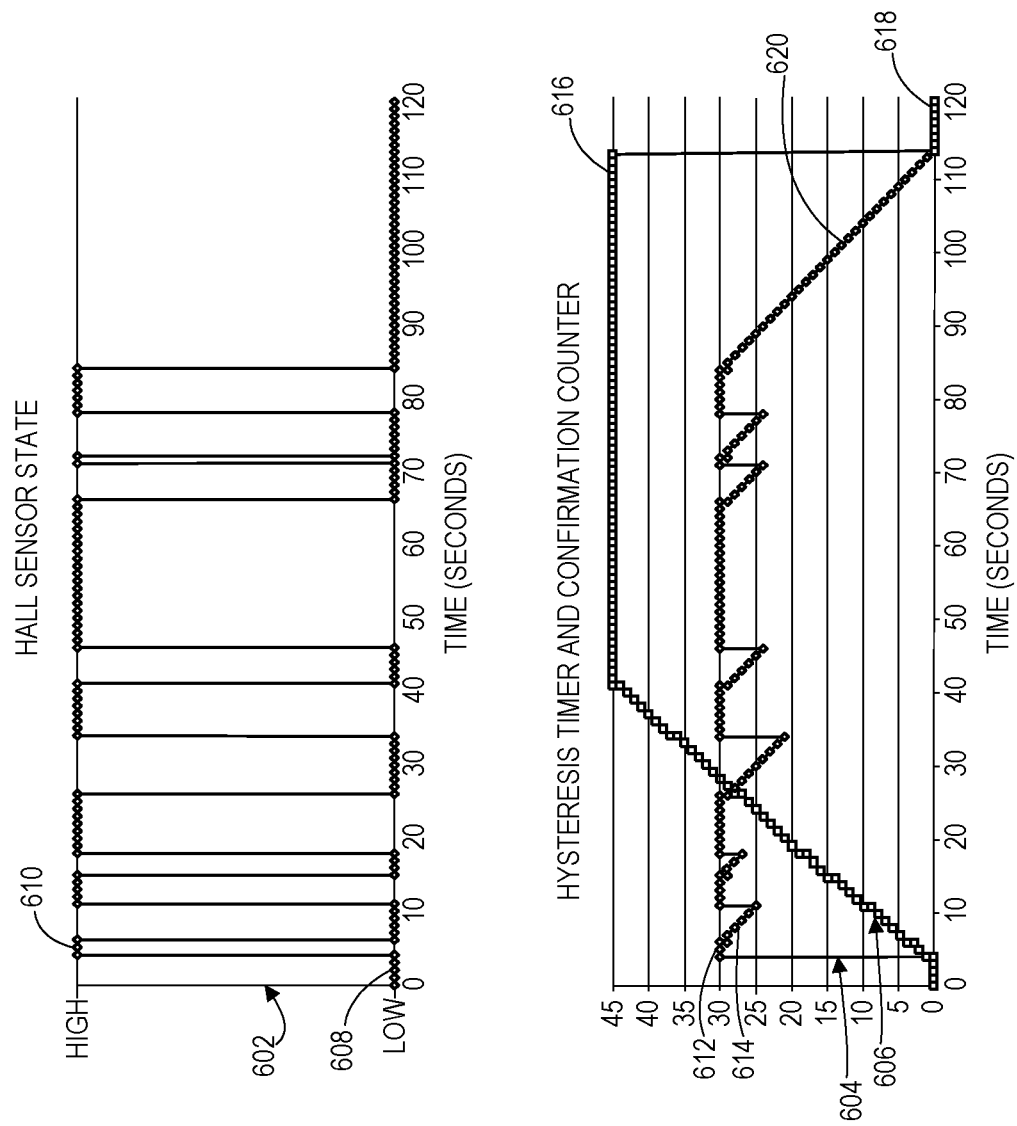
FIG. 6 shows a timeline of states of the magnetic sensor when encountering a magnetic disturbance and shows corresponding timelines of a hysteresis timer and a confirmation counter that result in entry to and exit from an exposure mode of operation.

FIG. 6 shows an example of a sensor signal 602 with respect to time and a corresponding example of both a hysteresis timer 604 and a confirmation timer/counter 606. The sensor signal 602 has both a LOW/OFF state 608 and a HIGH state 610. The HIGH state 610 suggests the presence of a magnetic field, as the sensor signal 602 remains in the LOW state 608 when no magnetic field is present. When a patient enters and exits the MRI scan room, as well as while mostly stationary in the MRI scan room, the sensor 210 may produce a signal 602 that toggles between the HIGH state 610 and the LOW state 608 as shown. Thus, it is not satisfactory to simply toggle the exposure mode on and off in accordance with the state of the signal 602. Instead, the goal is to have the exposure mode persist for at least the entire time the patient is in the MM scan room.

One example of doing so involves the controller 204 using a hysteresis timer 604 and a confirmation timer/counter 606. The hysteresis timer 604 is set to a start value 612, in this example 30 seconds, each time the controller 204 sees a HIGH signal value 610 when polling the sensor 210 to begin an entry test cycle. The hysteresis timer 604 is adjusted toward a stop value by a unit, in this example decremented one second toward the stop value of zero, each time the controller 204 sees a LOW signal value 608 when polling the sensor 210. The adjustment to the hysteresis timer 604 is evident from the diagonal sections 614 of timer 604 occurring during the LOW sensor states 608. While there is a 30 second span from the start value 612 to the stop value with 1 second decrements, it will be appreciated that other values may be used instead. However, a 30 second span is believed to be effective in many cases.

Meanwhile, the controller 204 adjusts the confirmation counter/timer 606 by a unit toward a target value each time the controller 204 polls the sensor 210. In this particular example, the controller 204 increments the confirmation counter/timer 606 by 1 second, starting from zero, toward the target value 616 of 45 seconds. The target value 616 could be some other value, but 45 seconds is believed to be effective in many cases. The controller 204 continues to increment the confirmation counter/timer 606 until either reaching the target value 616 or until the hysteresis timer 604 has fallen to zero. If the hysteresis timer 604 falls to zero before the confirmation counter/timer 606 has reached the target value 616, then the controller 204 does not switch to the exposure mode yet. However, as soon as the sensor signal 602 goes to HIGH 610, the hysteresis counter 604 and confirmation counter/timer 606 start again at the respective start values in another attempt to meet the entry criteria of the confirmation counter/timer 606 reaching the target value 616.

Once the confirmation counter/timer 606 does reach the target value 616, the controller 204 begins an exit test cycle by continuing to periodically poll the sensor 210 and adjust the hysteresis timer 604 by 1 unit of time toward the stop value (e.g., decrement by one second) during a LOW state 608 and set the hysteresis timer 604 back to the start value 612 during a HIGH state 610. The confirmation counter/timer 606 is maintained at the target value 616 as the exposure mode continues regardless of the fluctuations or even steady drops as shown at 620 in the hysteresis timer 604. However, once the hysteresis timer 604 reaches zero during the exit test cycle, the confirmation counter/timer 606 is cleared back to the start value (e.g., zero) and the controller 204 switches back to the normal mode of operation.

Figure 7:
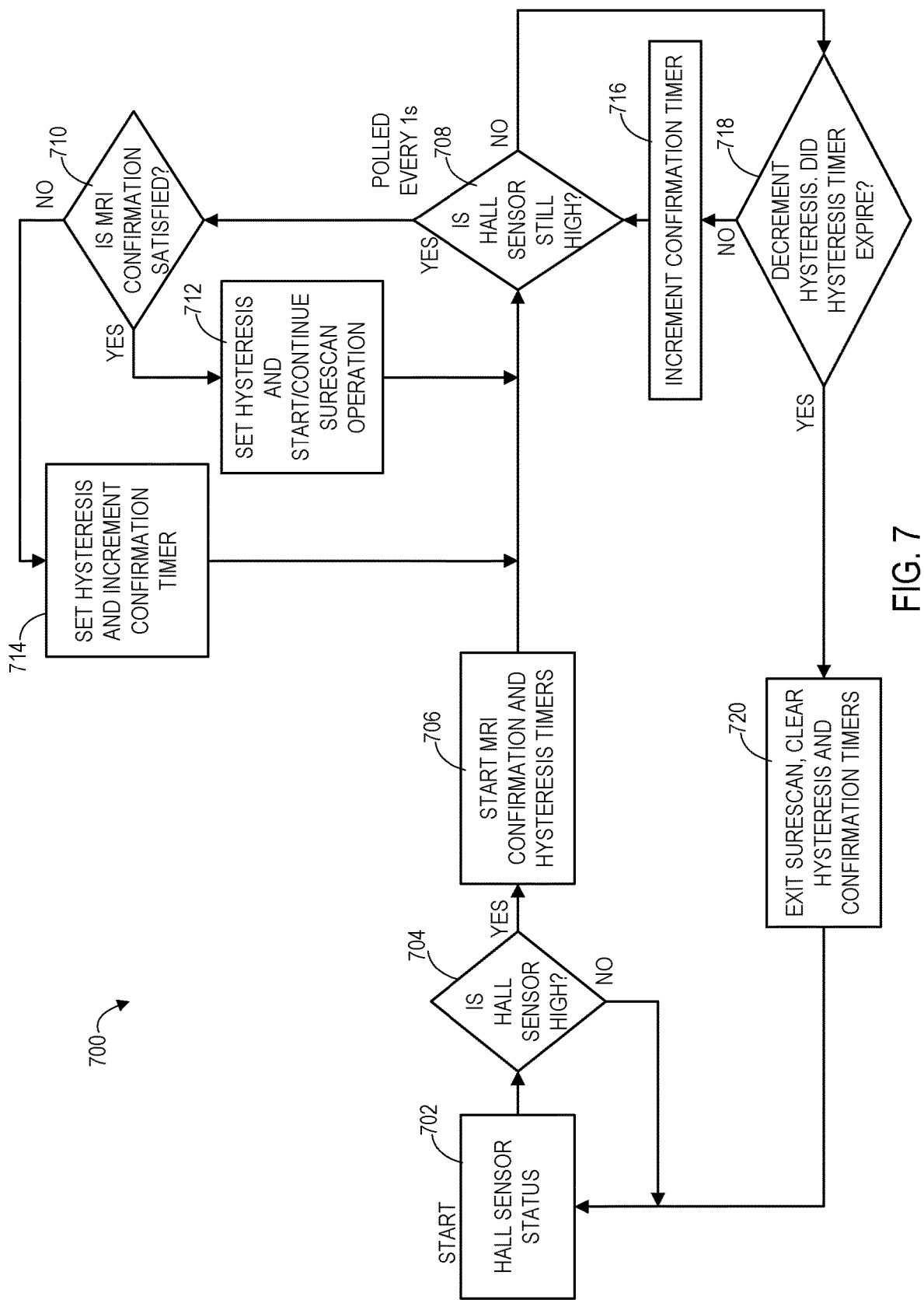
FIG. 7 shows a first example of operations that may be performed by an implantable medical device to implement the hysteresis timer and confirmation counter in order to automatically enter and exit an exposure mode of operation.

A first example 700 of operations performed by the controller 204 to implement the hysteresis timer 604 and the confirmation counter/timer 606 and to bring about the automatic switching between normal and exposure modes of operation is shown in FIG. 7. Initially, the controller 204 obtains the status of the sensor 210 at an operation 702. The controller 204 then determines whether the signal from the sensor 210 suggests the presence of a magnetic disturbance (i.e., is HIGH) at a query operation 704. If the status is not HIGH, then the controller 204 continues periodically polling the sensor 210. If the status is HIGH, then the controller 204 starts the confirmation and hysteresis timers at the operation 706 by setting the hysteresis timer to the hysteresis start value and incrementing the confirmation timer from the confirmation start value.

The controller 204 begins the entry test cycle by continuing to periodically poll the sensor 210 at the query operation 708 to determine if the sensor signal is HIGH. If the sensor signal is HIGH, then the controller 204 detects whether the entry criteria for switching to or maintaining the exposure mode of operation has been met at a query operation 710. Here, the controller 204 is determining if the confirmation counter/timer has reached the target value. If the criteria has been met, then the controller 204 sets the hysteresis timer back to the start value and switches to exposure mode if currently in entry test cycle of the normal mode or maintains exposure mode if already in the exit test cycle of the exposure mode at an operation 712. If the criteria have not been met, meaning the confirmation counter/timer has not yet reached the target value, then the controller 204 sets the hysteresis timer back to the start value and adjusts the confirmation timer by a unit toward the target value (i.e., increments by one second) at an operation 714.

Returning to the query operation 708, where the sensor signal is not HIGH, the controller 204 then adjusts the hysteresis timer by one unit of time toward the stop time (i.e., decrements by one second) and determines whether the hysteresis timer has expired by reaching the stop value (i.e., zero) at the query operation 718. If the hysteresis timer has not expired, then the controller 204 increments the confirmation timer at an operation 716 and then continues to periodically poll the sensor 210 at the query operation 708. If the hysteresis timer has expired, then the controller 204 exits from the exposure mode if currently in the exit test cycle of the exposure mode at an operation 720. Regardless of the current mode, the controller 204 also clears the hysteresis timer and the confirmation counter/timer at the operation 720, and then proceeds to obtain the sensor status again at the operation 702.

Figure 8:
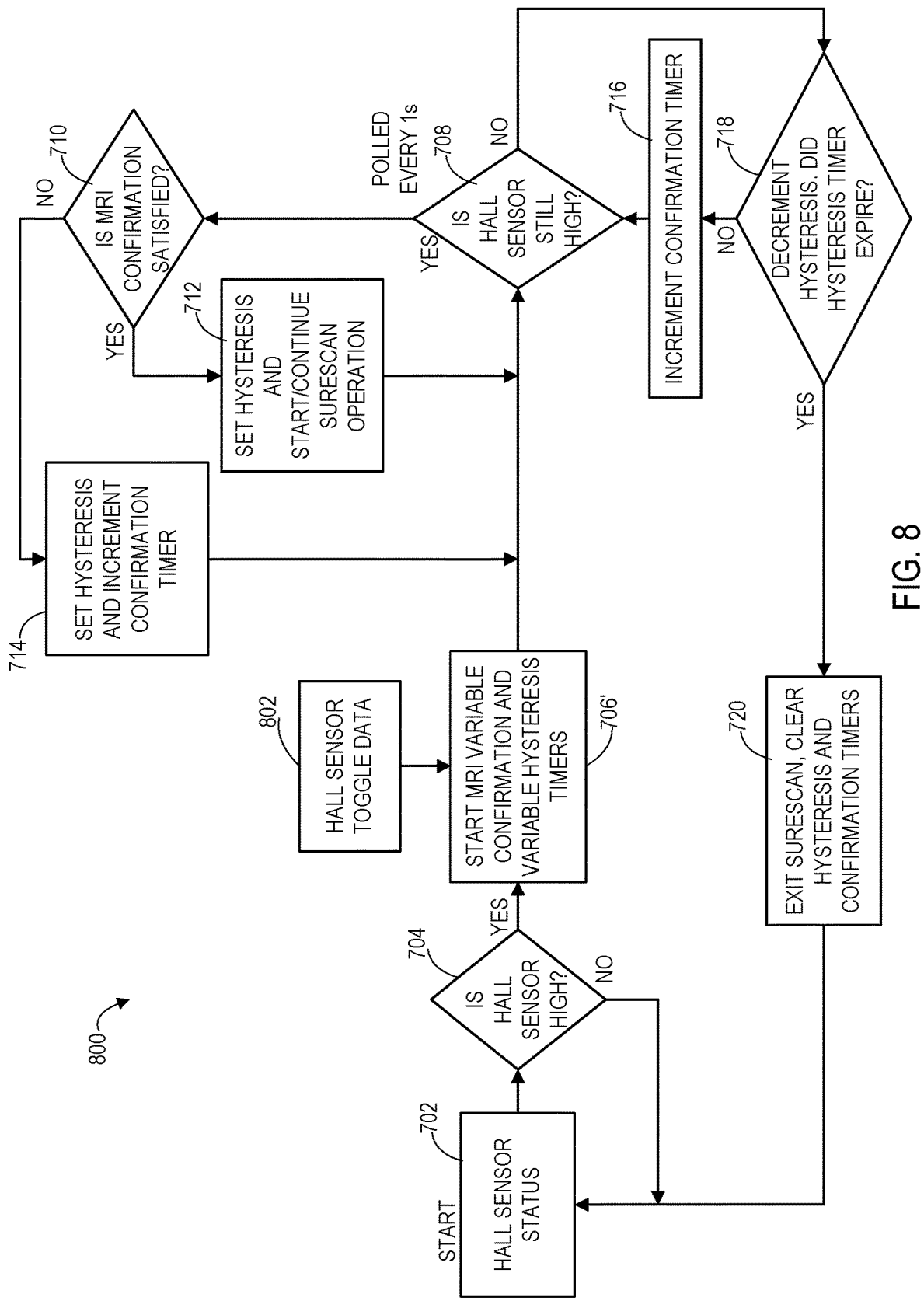
FIG. 8 shows a second example of operations that may be performed by an implantable medical device to implement the hysteresis timer and confirmation counter in order to automatically enter and exit an exposure mode of operation, where the hysteresis timer and/or confirmation counter may be variable.

FIG. 8 shows a second example 800 of using the hysteresis timer and the confirmation counter/timer to allow for automatic switching to and from an exposure mode of operation. The example 800 is identical to the example 700 of FIG. 7 discussed above, except that in the example 800, the hysteresis start value and the confirmation target value are dynamically assigned rather than being a pre-defined value that is used on every entry test cycle. Thus, after the controller 204 has detected a HIGH signal value from the sensor 210 at the query operation 704, the controller 204 accesses sensor toggle data 802 when deciding what the hysteresis start value and/or confirmation counter/timer target value should be at the operation 706' for this particular entry test cycle. For example, the sensor toggle data 802 may be data that the controller 204 has collected by polling the sensor 210 over some amount of time preceding the current entry test cycle.

Various situations may have occurred that result in the controller 204 choosing a particular value for the hysteresis timer. As one example, the controller 204 may determine that a particular hysteresis start value should be lower than on previous attempts where the confirmation timer achieved the target value only to have the hysteresis timer achieve zero in the shortest time possible thereafter and quickly terminate exposure mode, suggesting that this prior situation was not a real MM scan scenario and that the prior setting for the hysteresis timer was too high which allowed for an unnecessary switch to exposure mode. In such a scenario, the controller 204 may additionally or alternatively determine that the confirmation target value was too low on the prior attempts and set the confirmation target value to a higher value for the current attempt. Likewise, the controller 204 may make the opposite determination where it may have taken multiple resets of the confirmation counter to achieve the exposure mode but the exposure mode then lasted for a significant amount of time, suggesting that the hysteresis start value may have been too low and/or the confirmation target value may have been too high.

Figure 9:
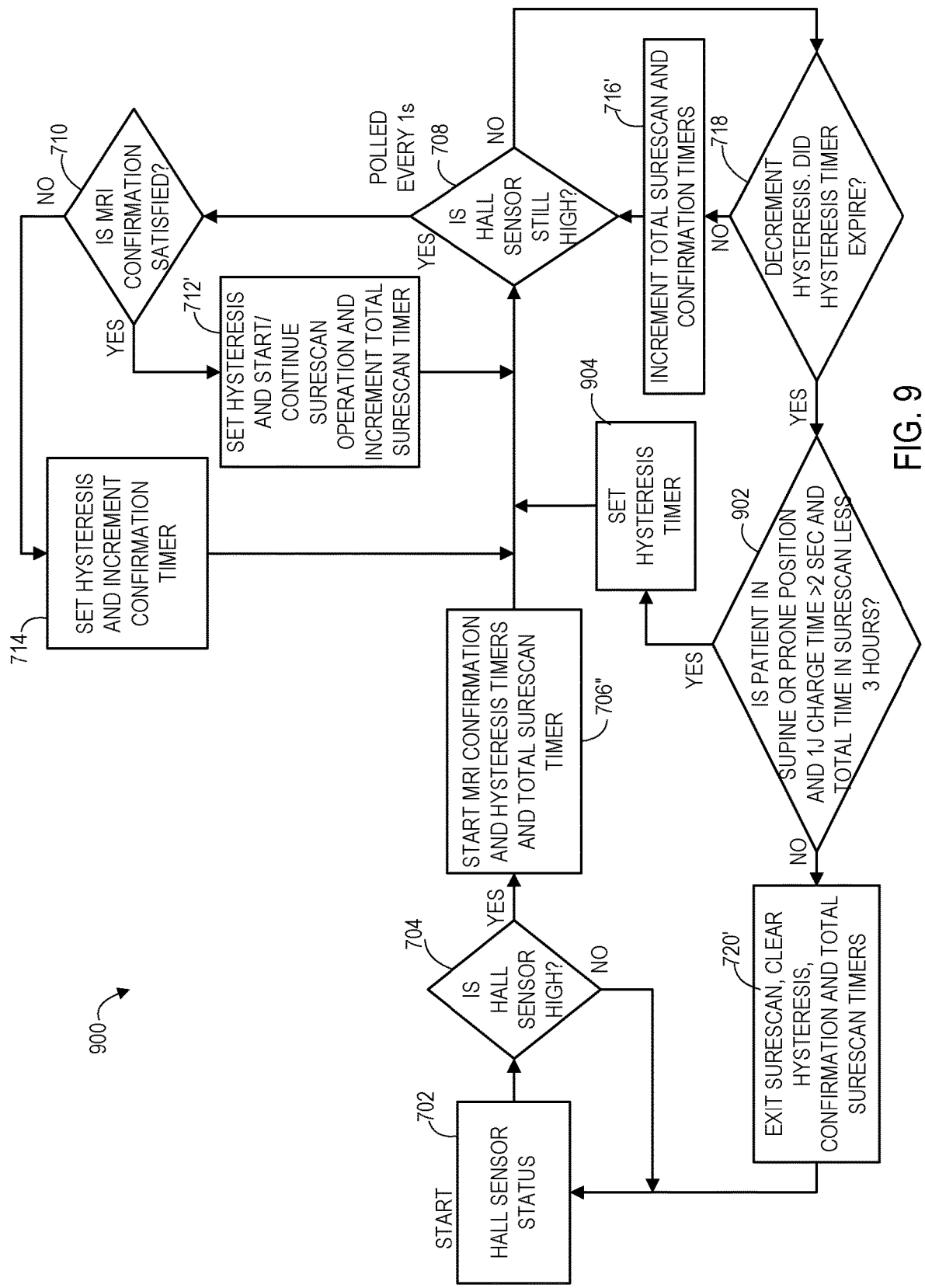
FIG. 9 shows a third example of operations that may be performed by an implantable medical device to implement the hysteresis timer and confirmation counter in order to automatically enter and exit an exposure mode of operation, where additional exit criteria are considered in order to automatically exit the exposure mode.

FIG. 9 shows a third example 900 of using the hysteresis timer and the confirmation counter/timer to allow for automatic switching to and from an exposure mode of operation. The example 900 is identical to the example 700 of FIG. 7 discussed above, except that in the example 900 there are additional exit criteria besides the hysteresis timer. The example 900 shows how one or more of three separate considerations may be a factor in deciding whether to exit the exposure mode of operation.

The first additional consideration relates to the total amount of time that the device has been in the exposure mode of operation. At each polling attempt of the sensor during the exposure mode of therapy, an exposure mode timer that keeps track of the total time in exposure mode is implemented. Thus, upon the controller 204 determining that there is a HIGH sensor signal at the query operation 704, the controller 204 then starts the exposure mode timer (referred to as a Total SureScan Timer) at a mode start value (e.g., zero) at an operation 706″ in addition to starting the hysteresis timer at the start value and incrementing the confirmation counter/timer. Then, when starting or continuing the exposure mode at the operation 712′, the controller 204 also adjusts the exposure mode timer by one unit of time toward or beyond a threshold value (e.g., increments by one second) in addition to setting the hysteresis timer back to the start value. Likewise, at an operation 716′, the controller 204 adjusts only the exposure mode timer by a unit of time when in the exposure mode and thus during the exit test cycle while the controller 204 adjusts only the confirmation counter/timer by a unit of time when in the normal mode and thus during the entry test cycle. The controller 204 thereby keeps track via the exposure mode timer of the total time in the exposure mode.

Upon the controller 204 determining that the hysteresis timer has expired by reaching zero at the query operation 718, the controller 204 then performs another query operation 902 before deciding to exit exposure mode or clear the confirmation counter when still in the entry test cycle of the normal mode. Various factors may be considered at the query operation 902. For instance, the controller 204 may determine whether the total time in exposure mode is less than the threshold. Additionally or alternatively, the controller 204 may determine whether the patient is in a prone or supine position by communicating with the position sensor 220. In the case of an IMD 102 with defibrillation capabilities, the controller 204 may determine whether the time to charge a high voltage source to a given amount of energy, such as one Joule, is greater than a threshold.

Any one of these factors may be considered alone at query operation 902 and if the controller 204 finds that the condition is met, the controller 204 sets the hysteresis timer back to the start value at an operation 904 to continue with the exposure mode or the attempt to enter the exposure mode. Alternatively, all of these additional factors may be considered together at the query operation 902 and if the controller finds that all of the conditions are met, then the controller 204 sets the hysteresis timer back to the start value at the operation 904. For example, in a non-defibrillation device, if both the total exposure mode time is less than the threshold (e.g., 3 hours) and the patient is in a prone or supine position or lateral decubitus, then the hysteresis timer is set back to the start value and the current mode carries on. As another example, in a defibrillation-capable device, if the total exposure mode time is less than the threshold, the patient is in the prone or supine position, and the charge time is greater than the charge time threshold, then the hysteresis timer is set back to the start value and the current mode carries on.

Once the controller 204 determines at the query operation 902 that the additional condition(s) is/are not met, then the controller 204 switches to the normal mode if currently in the exposure mode at the operation 720′. The controller 204 also clears the hysteresis timer, the confirmation counter/timer, and the exposure mode timer to prepare for future attempts to meet the entry criteria for switching back to the exposure mode.

While embodiments have been particularly shown and described, it will be understood by those skilled in the art that various other changes in the form and details may be made therein without departing from the spirit and scope of the invention.

What is claimed is:

1. An implantable medical device comprising:
a magnetic field sensor; and
a controller that selects between a normal mode of operation and an exposure mode of operation, the controller being configured to:
while in the normal mode of operation, communicate with the magnetic field sensor to detect over a first period of time a first aggregated amount of time that the magnetic field sensor signals that a magnetic disturbance is present;
compare the first aggregated amount of time to a first threshold, the first threshold comprising a threshold percentage of time for the first time period that is at least 3 percent and less than 100 percent; and
when the first aggregated amount of time exceeds the first threshold, then switch to the exposure mode of operation for the implantable medical device.

2. The device of claim 1, wherein the controller is further configured to:
while in the exposure mode of operation, detect over a second period of time a second amount of time that the magnetic field sensor continuously signals that the magnetic disturbance is not present;
compare the second amount of time to a second threshold; and
when the second amount of time exceeds the second threshold, switch to the normal mode of operation for the implantable medical device.

3. The device of claim 2, wherein the second threshold is equal to 30 seconds.

4. The device of claim 1, wherein the threshold percentage is 3% and the first time period is 60 seconds.

5. The device of claim 1, wherein the magnetic field sensor is a Hall Effect sensor.

6. A method of switching between a normal mode of operation and an exposure mode of operation for an implantable medical device, comprising:
the implantable medical device, while in the normal mode of operation, detecting over a first period of time a first aggregated amount of time that a magnetic field sensor signals that a magnetic disturbance is present;
comparing the first aggregated amount of time to a first threshold, the first threshold comprising a threshold percentage of time for the first time period that is at least 3 percent and less than 100 percent; and when the first aggregated amount of time exceeds the first threshold, switching to the exposure mode of operation for the implantable medical device.

7. The method of claim 6, further comprising:

the implantable medical device, while in the exposure mode of operation, detecting over a second period of time a second amount of time that the magnetic field sensor continuously signals that the magnetic disturbance is not present;

comparing the second amount of time to a second threshold;

when the second amount of time exceeds the second threshold, then switching to the normal mode of operation for the implantable medical device.

8. The method of claim 6, wherein the threshold percentage is 3%.

* * * * *